(12) United States Patent
Umebayashi et al.

(10) Patent No.: US 12,207,993 B2
(45) Date of Patent: Jan. 28, 2025

(54) METHOD FOR PRODUCING CUFFS FOR WEARABLE ARTICLE

(71) Applicant: ZUIKO CORPORATION, Osaka (JP)

(72) Inventors: Toyoshi Umebayashi, Osaka (JP); Hideki Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 210 days.

(21) Appl. No.: 17/928,669

(22) PCT Filed: Jun. 4, 2021

(86) PCT No.: PCT/JP2021/021329
§ 371 (c)(1),
(2) Date: Nov. 30, 2022

(87) PCT Pub. No.: WO2021/251286
PCT Pub. Date: Dec. 16, 2021

(65) Prior Publication Data
US 2023/0181380 A1  Jun. 15, 2023

(30) Foreign Application Priority Data

Jun. 10, 2020 (JP) ................................ 2020-100657

(51) Int. Cl.
*A61F 13/15* (2006.01)
(52) U.S. Cl.
CPC .............................. *A61F 13/15601* (2013.01)
(58) Field of Classification Search
CPC .......... A61F 13/15601; A61F 13/15609; A61F 13/15593; A61F 13/15699; A61F 13/15739
See application file for complete search history.

(56) References Cited

U.S. PATENT DOCUMENTS

2008/0249495 A1* 10/2008 Di Virgilio ......... A61F 13/4755
604/385.01
2015/0342790 A1   12/2015 Helton et al.
(Continued)

FOREIGN PATENT DOCUMENTS

CN    101410077 A       4/2009
EP       677284 A1 * 10/1995  ....... A61F 13/15593
(Continued)

OTHER PUBLICATIONS

International Search Report for corresponding Application No. PCT/JP2021/021329, mailed Aug. 17, 2021.

*Primary Examiner* — George R Koch
(74) *Attorney, Agent, or Firm* — Renner, Otto, Boisselle & Sklar, LLP

(57) ABSTRACT

The present cuff manufacturing method includes: a step of sandwiching at least two continuous elastic members F between a first sheet and a second sheet; a step of thermally-bonding together the first sheet and the second sheet intermittently in the longitudinal direction to form thermally-bonded portions, thereby fixing the continuous elastic members, thus forming a laminate; a slit step of slitting the laminate along the longitudinal direction, thereby obtaining a pair of cuff members; a step of conveying the pair of cuff members so that a pair of edges, which have been produced by the slitting in the pair of cuff members, are spaced apart from each other; and a step of arranging the pair of cuff members on opposite edge portions of a crotch portion of a worn article, thereby forming cuffs.

4 Claims, 7 Drawing Sheets

(56) References Cited

U.S. PATENT DOCUMENTS

2017/0348159 A1 12/2017 Shimada et al.
2019/0076302 A1 3/2019 Yamada

FOREIGN PATENT DOCUMENTS

| EP | 3056176 B1 | 8/2016 |
| JP | 2008-136667 A | 6/2008 |
| JP | 2012-125454 A | 7/2012 |
| JP | 2017-516543 A | 6/2017 |
| WO | 2007/116346 A1 | 10/2007 |
| WO | 2016/076223 A1 | 5/2016 |
| WO | 2017/159498 A1 | 9/2017 |

* cited by examiner

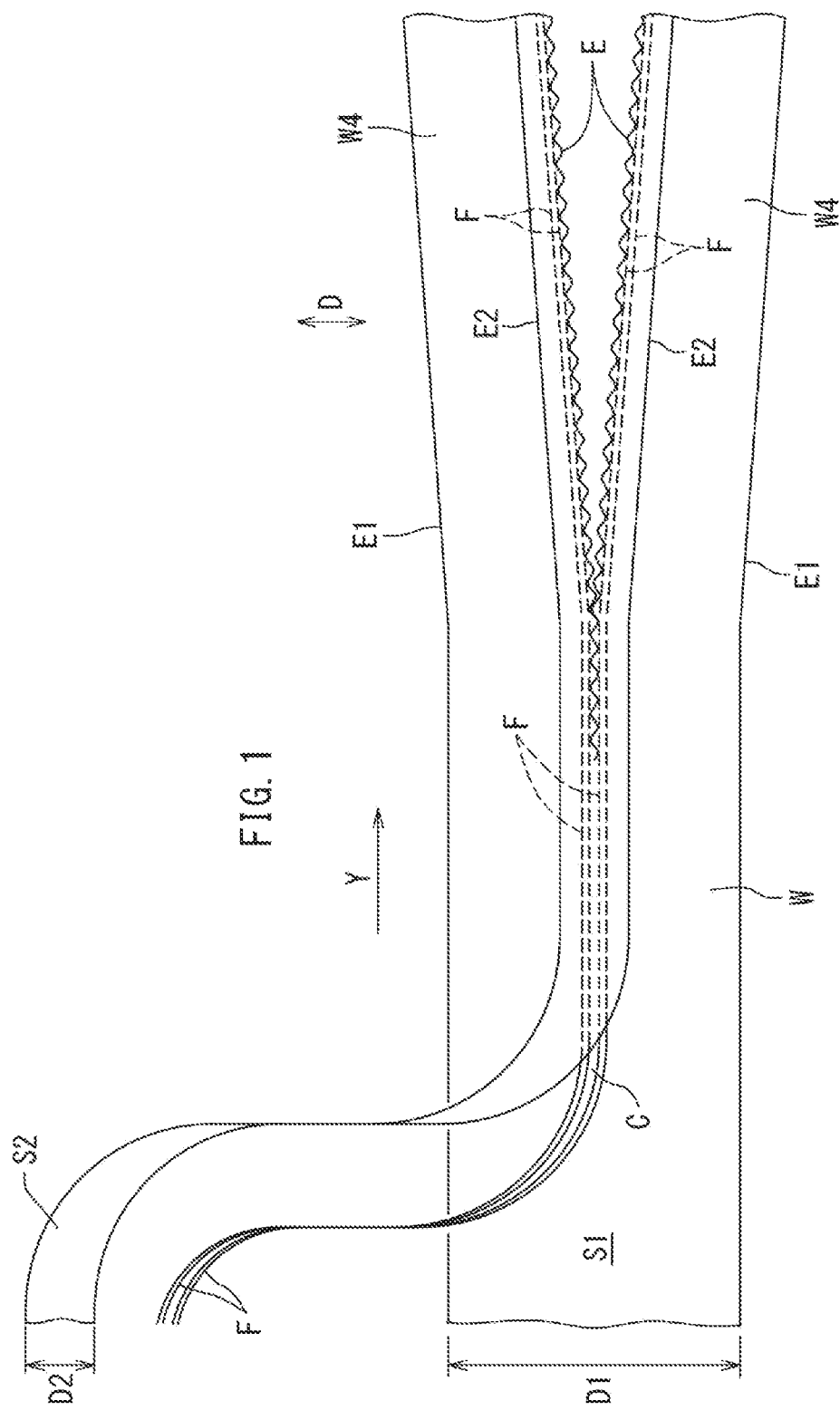

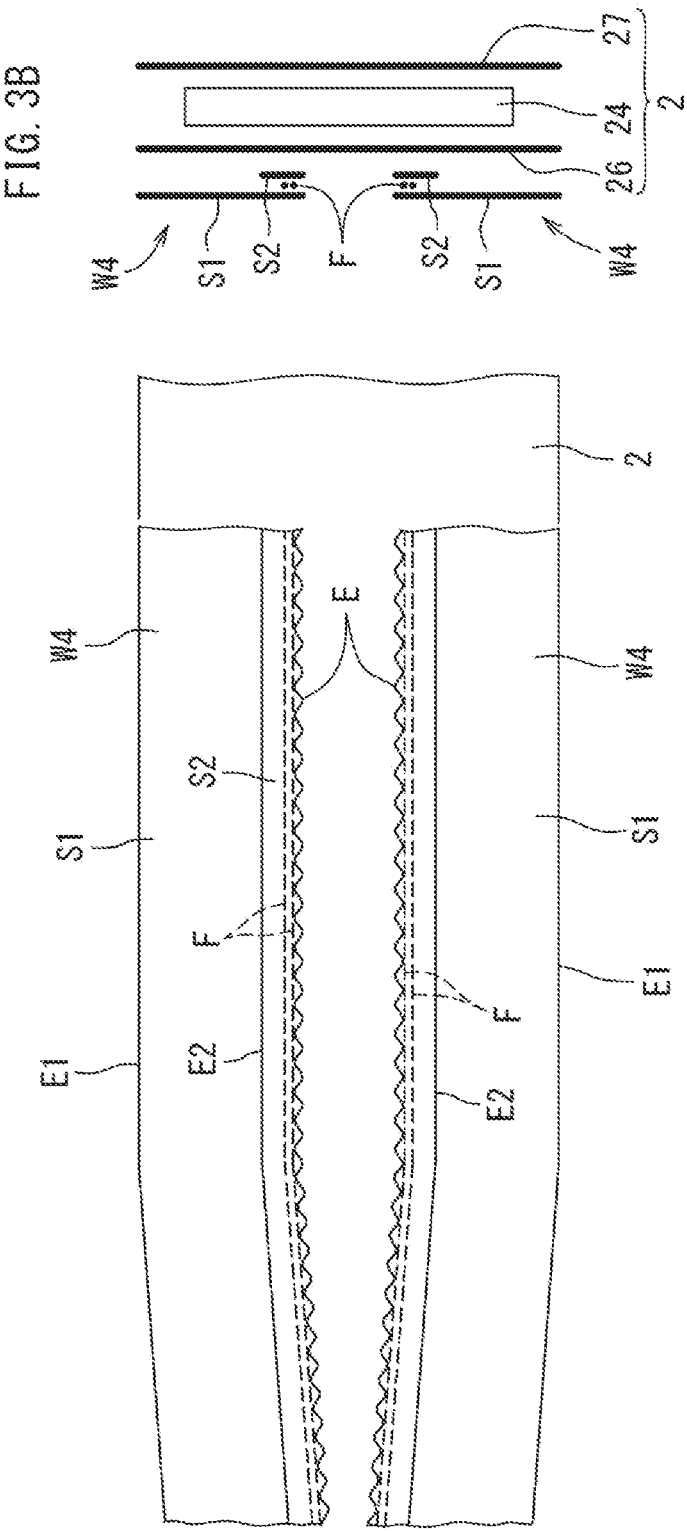

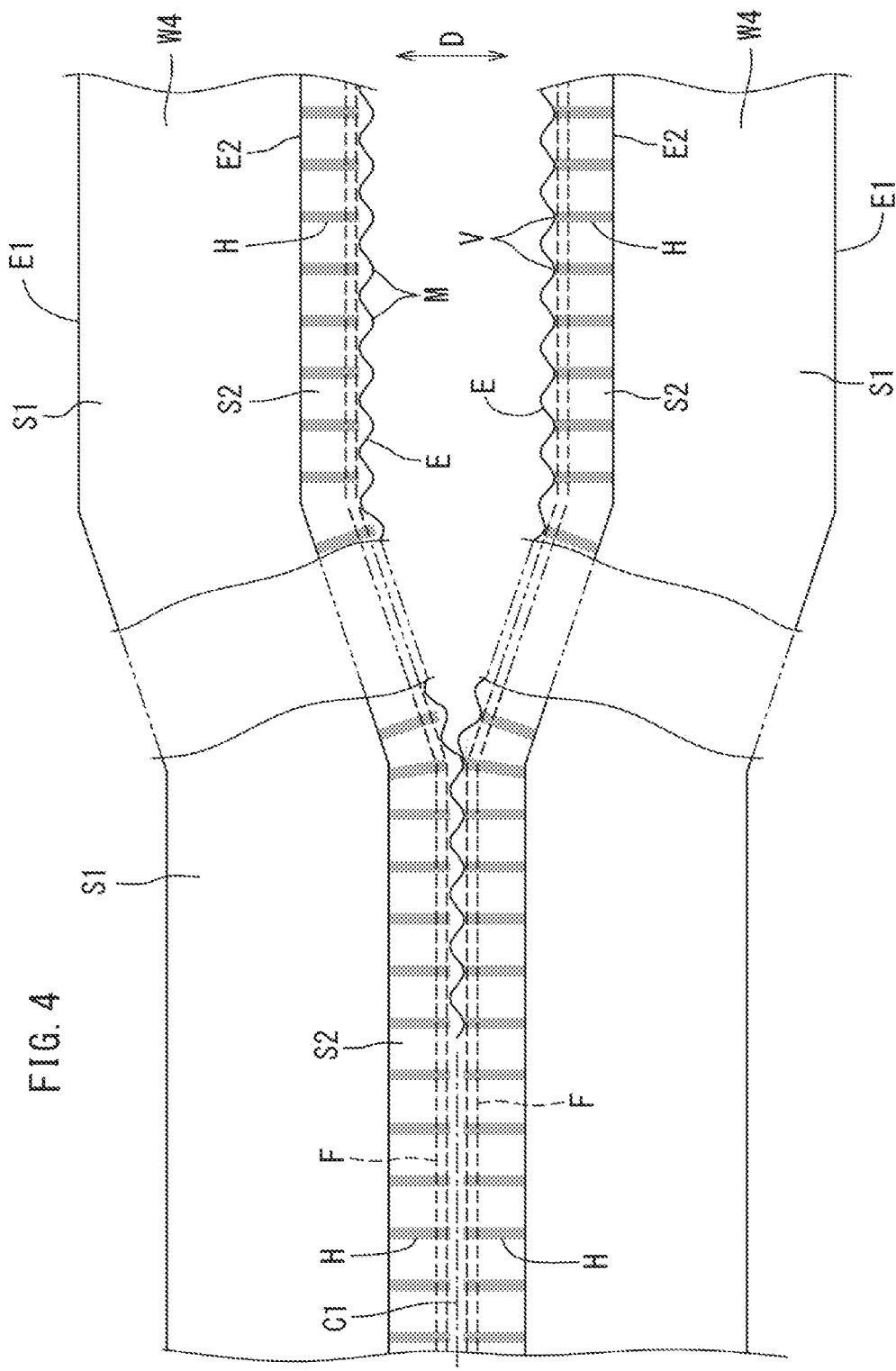

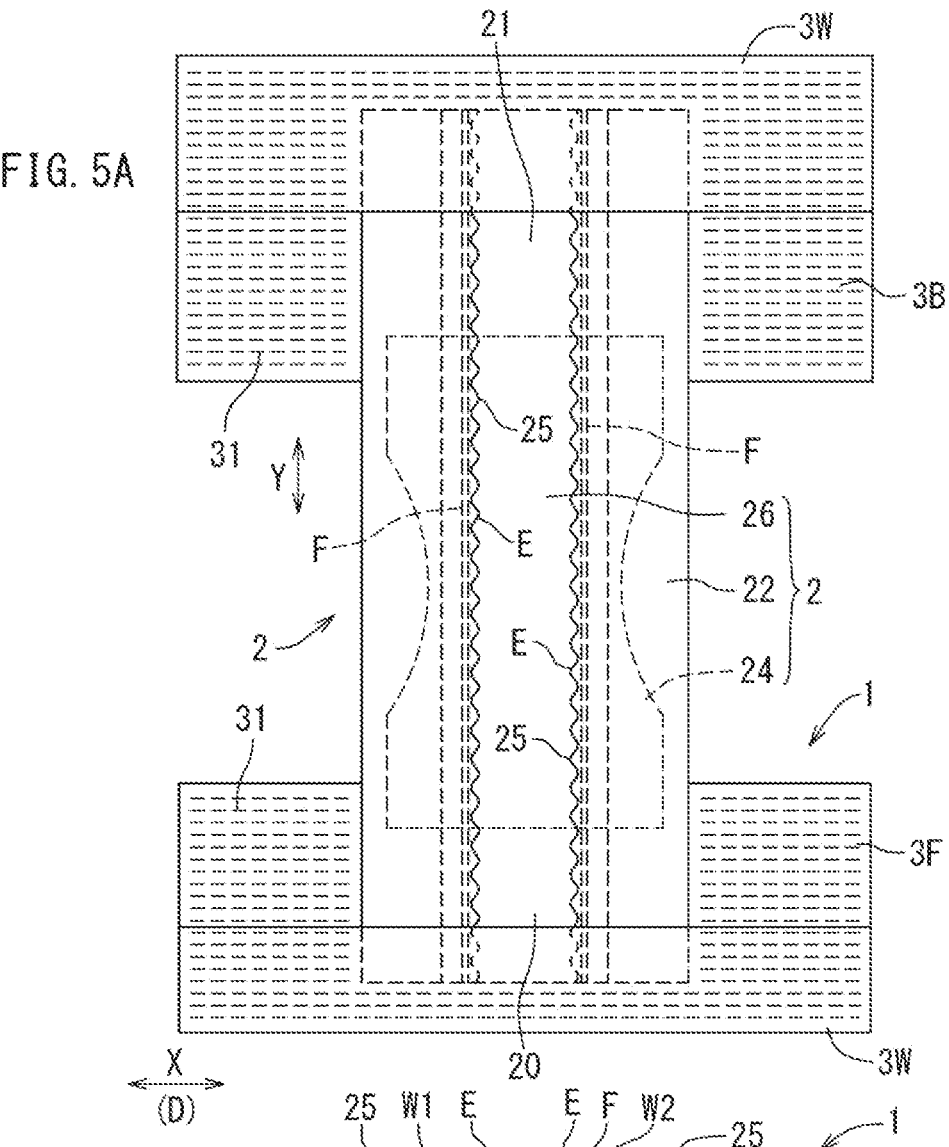
FIG. 5A
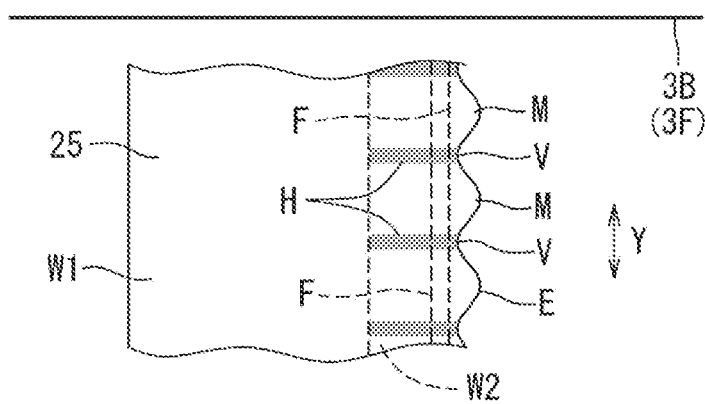
FIG. 5B
FIG. 5C

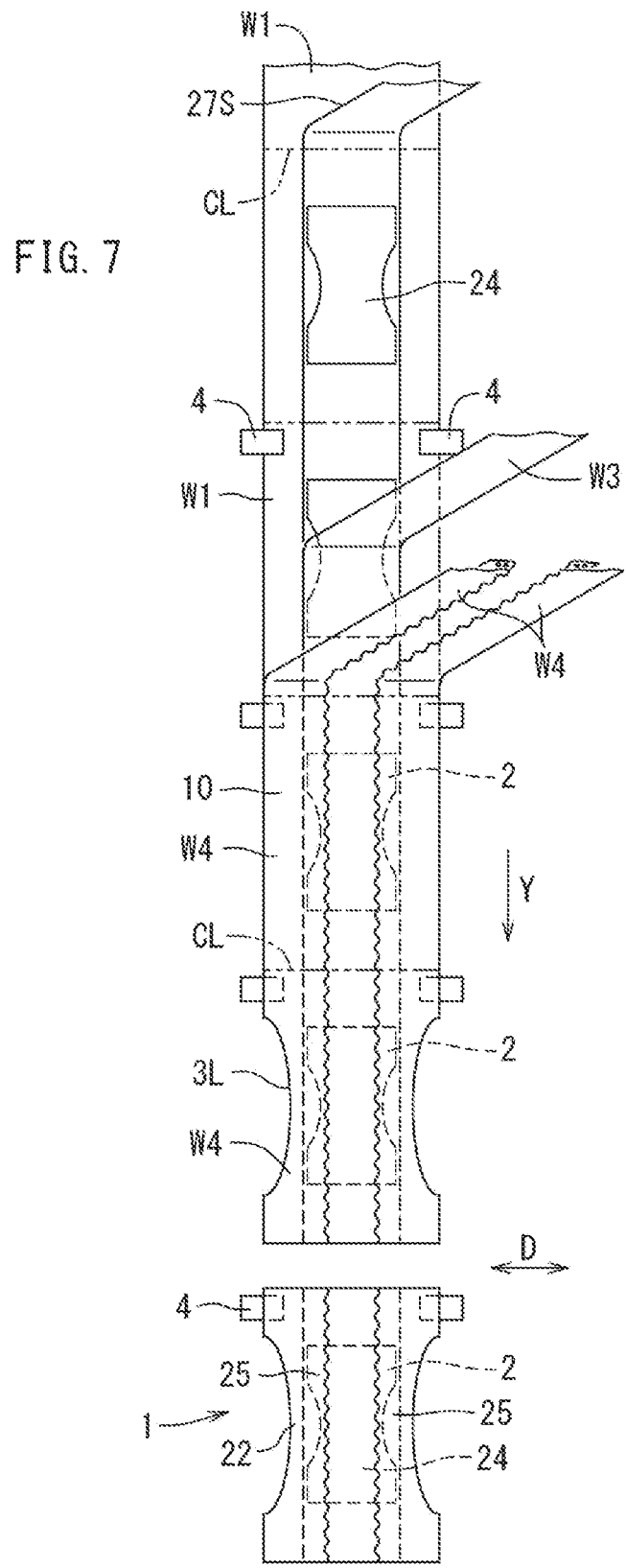

METHOD FOR PRODUCING CUFFS FOR WEARABLE ARTICLE

This application is a 371 of PCT/JP2021/021329, filing date Jun. 4, 2021.

TECHNICAL FIELD

The present invention relates to a method for manufacturing leak-proof walls (three-dimensional gathers) called cuffs in worn articles.

BACKGROUND ART

In recent years, worn articles (absorbent articles) such as disposable pants and diapers have been provided with a pair of cuffs to prevent side leakage of body fluids (the first patent document).

With the structure of the cuffs of the first patent document, the edge portion of the sheet is folded over, and elastic members are arranged between the sheet proximal portion and the folded edge portion. The sheet and the elastic members are bonded to each other with an adhesive. In recent years, however, efforts have been made to reduce the use of consumables such as an adhesive.

On the other hand, according to the second patent document identified below, the edge portion of the sheet is folded back against the proximal portion of the sheet, elastic members are sandwiched between the sheet proximal portion and the folded-back edge portion, and the sheet proximal portion and the folded-back edge portion are thermally bonded together, thus fixing the elastic members to the sheet.

CITATION LIST

Patent Document

[FIRST PATENT DOCUMENT] JP 2012-125454 A (front page)
[SECOND PATENT DOCUMENT] EP3 056 176 B1

SUMMARY OF INVENTION

With the invention of the second patent document, it is possible to avoid the use of an adhesive. With this conventional technique, however, since the edge portion is folded back, elastic members cannot be accurately guided when the elastic members are introduced between the sheet proximal portion and the folded-back edge portion, which may lead to breakage, etc., of the elastic members during the heat bonding process.

Thus, it is an object of the present invention to realize a method for manufacturing cuffs in worn articles, wherein it is possible to obtain a pair of cuffs without using an adhesive, and to prevent problems such as breakage of elastic members during the manufacture.

A cuff manufacturing method of the present invention includes:
 a step of conveying a first sheet S1 in a longitudinal direction Y;
 a step of conveying a second sheet S2 in the longitudinal direction Y;
 a step of sandwiching at least two continuous elastic members F between the first sheet S1 and the second sheet S2 with the first sheet S1 and the second sheet S2 facing each other and with the at least two continuous elastic members F spaced apart from each other and stretched;
 a step of thermally-bonding together the first sheet S1 and the second sheet S2 intermittently in the longitudinal direction Y to form thermally-bonded portions H, thereby fixing the at least two continuous elastic members F to the sheets S1, S2, thus forming a laminate W;
 a slit step of slitting the laminate W along the longitudinal direction Y between the at least two continuous elastic members F, thereby obtaining a pair of cuff members W4 in which at least one continuous elastic member F is sandwiched between the first sheet S1, which has been split in two, and the second sheet S2, which has been split in two;
 a step of conveying the pair of cuff members W4 so that a pair of edges E, which have been produced by the slitting in the pair of cuff members W4, are spaced apart from each other; and
 a step of arranging the pair of cuff members W4 on opposite edge portions of a crotch portion 22 of the worn article, thereby forming cuffs.

According to the present invention, the first sheet and the second sheet are thermally-bonded together, and there is no need to use an adhesive.

Moreover, since continuous elastic members are sandwiched between the first sheet and the second sheet, which are separate from each other, it is easy to introduce continuous elastic members F, and the continuous elastic members F will not inadvertently break in the thermal bonding step.

BRIEF DESCRIPTION OF THE DRAWINGS

FIG. 1 is a conceptual diagram showing the first half of a method of manufacturing cuffs, showing one embodiment of the present invention.

FIG. 3A and FIG. 3B are a plan view and a cross-sectional view, respectively, showing the step of laminating a cuff member on an absorbent core.

FIG. 4 is an enlarged plan view showing a welded portion.

FIG. 5A and FIG. 5B are a schematic plan view and a cross-sectional view, respectively, showing an example of a worn article, and FIG. 5C is a partial enlarged view of a cuff.

FIG. 7 is a plan view showing an example of the step of arranging cuffs on a worn article.

DESCRIPTION OF EMBODIMENTS

Figure 2B:
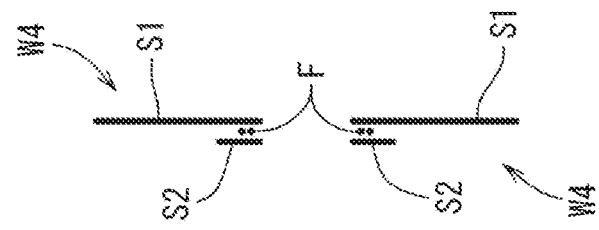
FIG. 2A and FIG. 2B are plan and end views of the second half thereof.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Hereinafter, an example of the structure of a worn article 1 will be described with reference to the drawings, prior to the description of a manufacturing method according to Embodiment of the present invention.

As shown in FIG. 5A and FIG. 5B, the worn article 1 of this example includes an absorbent body 2 and front and rear around-torso portions 3F, 3B. The absorbent body 2 has a front portion 20, a back portion 21, and a crotch portion 22. The front portion 20 covers the front torso (the front portion of the torso) of the wearer. The back portion 21 covers the rear torso (the rear portion of the torso) of the wearer. The crotch portion 22 covers the crotch of the wearer between the front portion 20 and the back portion 21.

The crotch portion 22 continuous with the front portion 20 and the back portion 21, and the absorbent body 2 is long in the lengthwise direction (the longitudinal direction) Y, which is perpendicular to the girth direction X.

In FIG. 5A, the present worn article 1 is worn with the crotch portion 22 folded in two along an imaginary line parallel to the girth direction X (the width direction D). As a result, the end portions, i.e., the sides, of the front and rear girth portions 3F, 3B in the around-torso direction X overlap each other.

As shown in FIG. 5B, the absorbent body 2 is provided with an absorbent core 24. This absorbent core 24 absorbs body fluids. The absorbent core 24 is sandwiched between a top sheet 26 and a back sheet 27. The sheets 26, 27 and the absorbent core 24 are laminated to each other.

In FIG. 5B, the top sheet 26 is made of a thin liquid-permeable non-woven fabric and covers the skin surface of the absorbent core 24. A pair of cuffs 25 are provided on this top sheet 26.

In the present invention, the "skin-contact surface" refers to an inner surface that directly or indirectly contacts the skin of the wearer when the diaper is worn, and directly or indirectly opposes the skin of the wearer.

The back sheet 27 covers the non-skin-contact surface of the absorbent core 24 and is made from a liquid-impermeable resin sheet. An air-permeable external non-woven fabric (not shown) is bonded and laminated to the non-skin-contact surface of the back sheet 27.

In the present invention, the "non-skin-contact surface" refers to an outer surface, opposite to the skin-contact surface, that does not contact the skin of the wearer when the diaper is worn, and does not oppose the skin of the wearer.

The front and rear around-torso portions 3F, 3B may be provided with elastic members 31 for the waist and for the hip.

A pair of cuffs 25 are arranged on the top sheet 26 spaced apart from each other in the width direction D. One of the pair of cuffs 25 is arranged at one edge portion of the crotch portion 22 of the worn article 1 and another of the pair of cuffs 25 is arranged at another edge portion of the crotch portion 22 of the worn article 1. The edges of the cuffs 25 may be secured to the edges of the absorbent body 2.

The cuffs 25 are formed with at least one elastic member F sandwiched between a first web W1 and a second web W2 of a predetermined length. The width of the second web W2 is smaller than the width of the first web W1. Note that the elastic members may be, for example, a plurality of rubber threads as well as threads or strips of material including urethane foam.

The first web W1 may be secured to the edge of the top sheet 26 or the back sheet 27. On the other hand, the elastic members F are under a tension in the unfolded state of FIG. 5A. Because of such a structure, when the worn article 1 is worn, the elastic members F contract, thereby raising the first web W1 and the second web W2 and forming gathers in the second web W2, and the cuffs 25 form three-dimensional gathers (leak-proof walls), which are well known in the art.

The inner edges E where the pair of cuffs 25 face each other may each be formed in a corrugated shape (a wave shape) with valley portions V and mountain portions M alternating with each other as shown in an enlarged view in FIG. 5C. For each cuff of the pair of cuffs 25, the valley portions V are closer to the elastic members F included in the cuff, while the mountain portions M are farther away from the elastic members F included in the cuff 25.

In FIG. 5C, thermally-bonded portions H where the first web W1 and the second web W2 of the cuff 25 are thermally-bonded together are shown colored in gray. As shown in this figure, the thermally-bonded portions H are formed intermittently in the longitudinal direction Y. The thermally-bonded portions H are formed so as to include a portion of the elastic members F and to be located at the valley portions V so that the mountain portions M are not welded. Thus, the first web W1 and the second web W2 do not become hard at the mountain portions M, thereby realizing a good feel against the skin.

Next, an example of a method for manufacturing the cuffs 25 will be described with reference to FIG. 1 to FIG. 3.

In FIG. 1, a first sheet S1 and a second sheet S2 are conveyed in the longitudinal direction Y. The first and second sheets S1, S2 are continuous in the longitudinal direction Y, and the width D1 of the first sheet S1 is larger than the width D2 of the second sheet S2. Note that the first sheet S1 and the second sheet S2 are continuous non-woven fabrics and are processed into the first web W1 and the second web W2, respectively.

Next, at least two continuous elastic members F are sandwiched between the first sheet S1 and the second sheet S2 with the first sheet S1 and the second sheet S2 facing each other and with the at least two continuous elastic members F spaced apart from each other and stretched in the longitudinal direction Y. The second sheet S2 is laid over the central portion C of the first sheet S1 in the width direction D. In this process, the sheets S1 and S2 are laid over each other so that the pair of outer edges E1 of the first sheet S1 and the pair of outer edges E2 of the second sheet S2 are parallel to each other.

Then, the first sheet S1 and the second sheet S2 are thermally-bonded together intermittently in the longitudinal direction Y to form thermally-bonded portions H (shown in gray in FIG. 4), thereby fixing the at least two continuous elastic members F to the sheets S1, S2, thus forming a laminate W. Note that the thermally-bonded portions will be described in detail later.

Then, a slit step is performed to split the laminate W in two. In this slit step, the laminate W is slit along the longitudinal direction Y between the at least two continuous elastic members F, thereby obtaining a pair of cuff members W4. Each cuff member W4 includes at least one continuous elastic member F sandwiched between the first sheet S1, which has been split in two, and the second sheet S2, which has been split in two.

In the slit step, the laminate W is slit so that the pair of cuff members W4, which have been split in two, include an equal number of continuous elastic members F. The laminate W may be slit so that the edge E of the cuff member W4 is corrugated.

Figure 2A:
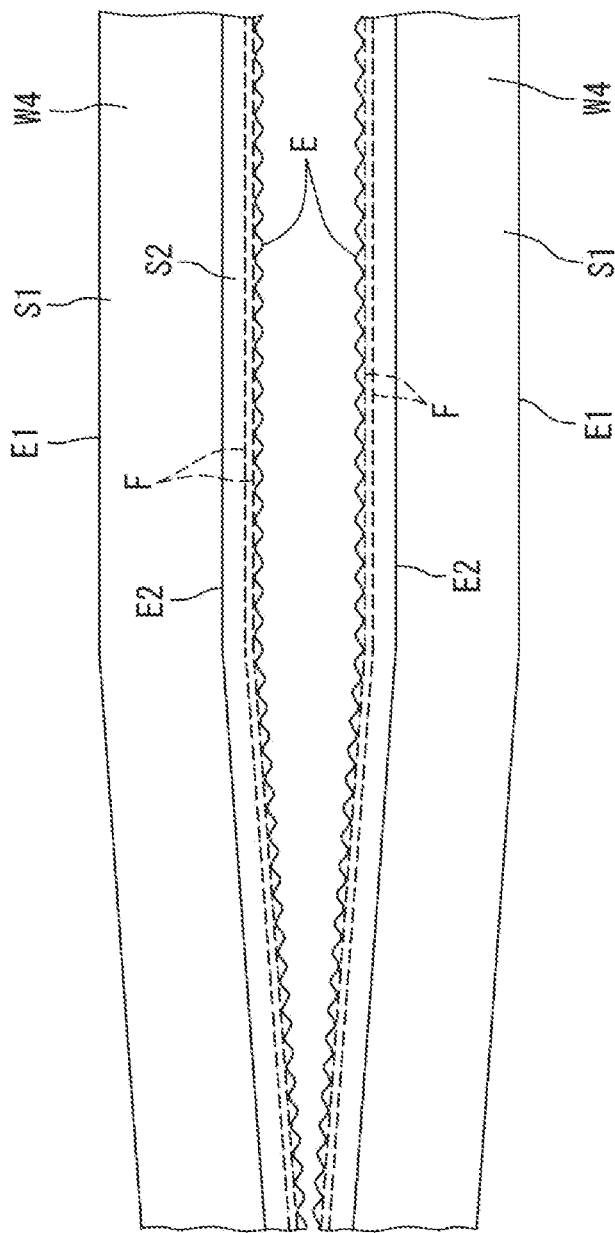

Then, a gap-widening step is performed. That is, the pair of cuff members W4 are conveyed while widening the gap between the pair of cuff members W4, W4 so that one edge E of the one cuff member W4 and the other edge E of the other cuff member W4 are spaced apart from each other after the pair of edges E, E have been produced by the slitting. After the gap is widened in the gap-widening step, the pair of cuff members W4 are conveyed so that the pair of outer edges E1, E1 are parallel to each other as shown in FIG. 2A.

The pair of cuff members W4 thus produced are laminated to the absorbent body 2 so that the second sheet S2 is sandwiched between the first sheet S1 and the top sheet 26 of the absorbent core 24, as shown in FIG. 3A and FIG. 3B. In this process, the pair of outer edges E1 of the first sheet S1 are attached to the outer edges of the absorbent body 2, thereby producing a continuous sheet of the absorbent body 2.

After the attachment, the continuous material of the absorbent body 2 is cut into absorbent bodies 2 by the units of individual worn articles. The individual absorbent bodies 2 may be provided so as to bridge between the pair of around-torso portions 3F, 3B, as shown in FIG. 5A, for example. Thus, a pair of cuff members W4 are arranged at the opposite edges of the crotch portion 22 of the worn article 1 to form the cuff 25.

Note that as shown in FIG. 5A, the web 3W forming the around-torso portions 3F, 3B may be folded back so that the opposite end portions of the absorbent body 2 in the longitudinal direction Y are covered by the web 3W.

Next, the thermally-bonded portions H will be described with reference to an enlarged view of FIG. 4.

In FIG. 4, after the slit step, each thermally-bonded portion H includes two continuous elastic members F and extends up to the valley portion V of the inner edge E but does not extend up to the mountain portion M. That is, the pair of sheets S1, S2 may be slit so that the thermally-bonded portions H are located at the valley portions V. Therefore, the first sheet S1 and the second sheet S2 are not bonded to each other at the mountain portions M.

In FIG. 4, in order to realize such a configuration, the first sheet S1 and the second sheet S2 are thermally-bonded to each other in the thermal bonding step before the slit step so as to include the two continuous elastic members F and not include the center line C1 of the sheets. Note that the thermal bonding may be performed by ultrasonic bonding or by heat rollers.

As shown in FIG. 4, the thermally-bonded portions H described above are formed at two locations that are apart from each other with the center line C1 therebetween. In the slit step, the laminate W is slit so that a plurality of thermally-bonded portions H appear intermittently in the conveyance direction Y (the longitudinal direction Y) between the inner edges E, E formed by severing the laminate W in a corrugated shape and the pair of outer edges E2, E2 of the second sheet S2 to form the cuff members W4.

That is, the thermally-bonded portions H of FIG. 4 include thermally-bonded portions H arranged on one of the pair of cuff members W4 and thermally-bonded portions H arranged on the other one of the pair of cuff members W4. In the step of forming the laminate W, the laminate W is formed so that the first and second thermally-bonded portions H, H are spaced apart from each other in the width direction D, which is perpendicular to the longitudinal direction. The laminate W is slit between the first and second thermally-bonded portions H, which are spaced apart from each other, so that the edge E appears between the thermally-bonded portions H, H, thereby forming the pair of cuff members W4.

Now, the thermally-bonded portions H of FIG. 4 may be continuous in the width direction D so as to include the center line C1. In this case, the thermally-bonded portions H may be arranged between mountain portions M of the edge E so that the thermally-bonded portions H are not arranged at the mountain portions M. Then, the sheets S1, S2 are not thermally-bonded to each other at the mountain portions M, thereby realizing a good feel against the skin.

Note that the pitch of the thermally-bonded portions H in the longitudinal direction Y may be generally equal to or different from the wavelength of the waveform of the corrugated edges E, E.

Next, Embodiment 2 of the present invention will be described.

Figure 6A:
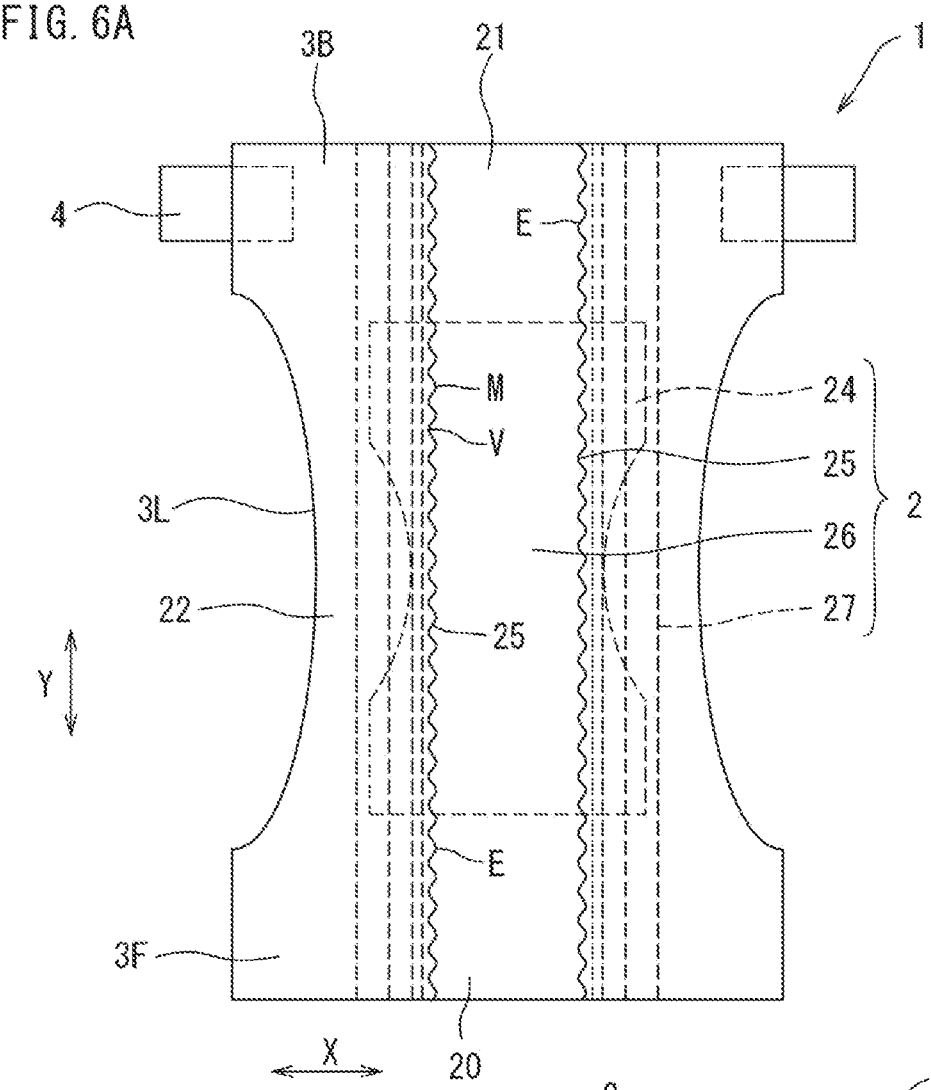
FIG. 6A and FIG. 6B are a schematic plan view and a cross-sectional view, respectively, showing another example of a worn article.

FIG. 6A to FIG. 7 show Embodiment 2.

Figure 6B:
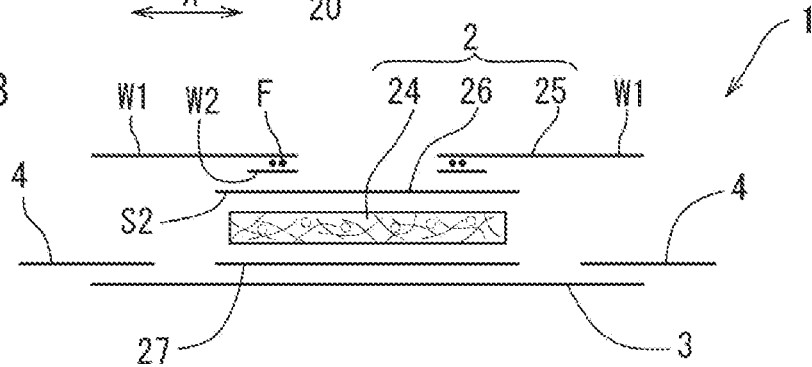

As shown in FIG. 6A and FIG. 6B, the pair of cuffs 25 are provided to extend from one end to the other end of a disposable diaper in the longitudinal direction Y and from one end to the other end in the girth direction X.

As shown in this example, narrowed portions to be leg holes may be formed in the cuffs 25 and the absorbent body 2. Note that where the worn article is a diaper, a tape material 4 coated with a fastening agent or a fastener material may be secured to the rear around-torso portion 3B.

Next, a method of this example for forming the cuffs 25 by arranging the cuff material W4 of FIG. 7 on the worn article 1 will be described. This example shows the case of so-called longitudinal flow.

In FIG. 7, a continuous sheet 27S of the back sheet 27 is arranged on the first web W1 (a non-woven fabric web), the absorbent core 24 may be arranged on the continuous sheet 27S and attached to the continuous sheet 27S. Then, the pair of tape materials 4 of FIG. 7 are attached to the first web W1, and further a liquid-permeable continuous web W3 to be the top sheet 26 is laminated so as to cover the absorbent core 24 and the continuous sheet 27S.

Thereafter, the pair of cuff members W4 to be the cuffs 25 (FIG. 6A) are laminated to produce an intermediate article 10 of the worn article. After the lamination, the first web W1 (a non-woven fabric web) and the cuff members W4 may be partially cut off to form portions to be leg holes 3L.

Then, in order to obtain individual worn articles 1 from the intermediate article 10 of FIG. 7, the intermediate article 10 is severed along an imaginary cut-off line CL extending in the width direction D perpendicular to the conveyance direction Y. Note that the intermediate article 10 is cut off between absorbent bodies 2, 2 adjacent to each other. Thus, the worn article 1 of FIG. 6A to FIG. 6B is obtained.

The specific embodiment described above includes an invention configured as follows.

In a preferred manufacturing method, in the slit step, the slitting is performed so that the edge E of the cuff member W4 is corrugated.

In this case, the corrugated edge E touches the skin of the wearer. This improves the feel against the skin and the texture.

More preferably, the corrugated edge E alternatingly includes valley portions V closer to the continuous elastic member F and mountain portions M farther away from the continuous elastic member F; and the slitting is performed so that thermally-bonded portions H are located at the valley portions V.

In this case, the thermally-bonded portions H that have been hardened by thermal bonding are absent at the mountain portions M, thereby further improving the feel against the skin.

Preferably, the width D1 of the first sheet S1 is larger than the width D2 of the second sheet S2; and in the sandwiching step, the second sheet S2 is laid over the central portion C of the first sheet S1 in the width direction D.

In this case, a pair of left and right cuffs are generally symmetrical.

More preferably, the sandwiching step is done so that the pair of outer edges E1 of the first sheet S1 and the pair of outer edges E2 of the second sheet S2 are parallel to each other.

In this case, a pair of left and right cuffs are in a symmetrical shape.

Preferably, the slit step is performed so that the pair of cuff members W4, which have been split in two, include an equal number of continuous elastic members F.

In this case, a pair of left and right cuffs are likely to evenly contact against the skin.

Any feature illustrated and/or depicted in conjunction with one embodiment or preferred embodiments may be used in the same or similar form in one or more of the other embodiments, and/or may be used in combination with, or in place of, the other embodiments.

While preferred embodiments have been described above with reference to the drawings, obvious variations and modifications will readily occur to those skilled in the art upon reading the present specification.

For example, one elastic member or three or more elastic members may be provided in each cuff.

The pair of edges produced by the slitting may be straight rather than corrugated.

Thus, such variations and modifications shall fall within the scope of the present invention as defined by the appended claims.

INDUSTRIAL APPLICABILITY

The present invention is applicable to the manufacture of diaper-type and pants-type disposable worn articles, etc.

REFERENCE SIGNS LIST

S1: First sheet, S2: Second sheet
1: Disposable worn article, 10: Intermediate article
2: Absorbent body, 20: Front portion, 21: Back portion, 22: Crotch portion
24: Absorbent core, 25: Cuff, 26: Top sheet, 27: Back sheet
3: External non-woven fabric, 3F, 3B: Around-torso portion, 3L: Leg hole
4: Tape material (fastening member)
C: Central portion, CL: Cut-off line, C1: Center line
D: Width Direction, D1, D2: Width
E: Edge, E1, E2: Outer edge
F: Continuous elastic member
H: Thermally-bonded portion, X: Around-torso portion, Y: Longitudinal direction
W: Laminate, W1: First web (non-woven fabric web), W3: Continuous web, W4: Cuff member
V: Valley portion, M: Mountain portion

The invention claimed is:

1. A method for manufacturing a cuff of a worn article, the method comprising:
a step of conveying a first sheet in a longitudinal direction;
a step of conveying a second sheet in the longitudinal direction;
a step of sandwiching at least two continuous elastic members between the first sheet and the second sheet with the first sheet and the second sheet facing each other and with the at least two continuous elastic members spaced apart from each other and stretched;
a step of thermally-bonding together the first sheet and the second sheet intermittently in the longitudinal direction to form thermally-bonded portions, thereby fixing the at least two continuous elastic members to the first and the second sheets, thus forming a laminate;
a slit step of slitting the laminate along the longitudinal direction between the at least two continuous elastic members, thereby obtaining a pair of cuff members,
each of the pair of cuff members having at least one continuous elastic member of the elastic members sandwiched between the first sheet, which has been split in two, and the second sheet, which has been split in two;
a step of conveying the pair of cuff members so that one edge of one of the cuff members and another edge of another of the cuff members are spaced apart from each other, the one edge and the other edge having been produced by the slit step; and
a step of arranging the cuff members on respective opposite edge portions of a crotch portion of the worn article, thereby forming the cuff on each of the opposite edge portions,
wherein:
a width of the first sheet is larger than a width of the second sheet,
in the sandwiching step, the second sheet is laid over a central portion of the first sheet in a width direction,
in the slit step, the slitting is performed so that the one edge and the other edge of the cuff members are corrugated,
the one edge and the other edge each alternatingly includes valley portions closer to the continuous elastic member and mountain portions farther away from the continuous elastic member; and
in the slit step, the slitting is performed so that, in a direction perpendicular to the longitudinal direction, the thermally-bonded portions extend from an outer edge side of the second sheet up to the valley portion of an inner edge but does not extend up to the mountain portion.

2. The manufacturing method according to claim 1, wherein:
the slitting is performed so that the thermally-bonded portions are located at the valley portions.

3. The manufacturing method according to claim 1, wherein the sandwiching step is done so that a pair of outer edges of the first sheet and a pair of outer edges of the second sheet are parallel to each other.

4. The manufacturing method according to claim 1, wherein the slit step is performed so that the pair of cuff members, which have been split in two, include an equal number of the at least one continuous elastic member.

* * * * *